United States Patent [19]
Carter

[11] Patent Number: 5,334,202
[45] Date of Patent: Aug. 2, 1994

[54] PORTABLE BONE DISTRACTION APPARATUS

[76] Inventor: Michael A. Carter, 22039 W. Rodeffer Pl., Saugus, Calif. 91350

[21] Appl. No.: 43,412

[22] Filed: Apr. 6, 1993

[51] Int. Cl.⁵ .......................... A61B 17/60; A61F 5/04
[52] U.S. Cl. ........................................ 606/58; 606/102
[58] Field of Search .................. 606/53, 54, 55, 57, 606/58, 102, 105, 86; 128/736, 630, 632, 637; 364/413.01, 413.02, 413.03

[56] References Cited

U.S. PATENT DOCUMENTS 4,096,857 6/1978 Cramer et al. ..................... 606/57

FOREIGN PATENT DOCUMENTS

1313437 5/1987 U.S.S.R. ............................... 606/86
994077 6/1965 United Kingdom ............... 606/102

*Primary Examiner*—Tamara L. Graysay
*Attorney, Agent, or Firm*—W. Norman Roth

[57] ABSTRACT

A portable bone distraction apparatus comprises a frame having a pair of relatively moveable parts which are respectively connectable to the bone parts on opposite sides of a break and tissue condition sensors positionable on opposite sides of a break. The sensors determine tissue conditions such as temperature or oxygen content. The apparatus includes a microprocessor control circuit which governs rate and frequency of distractions with automatic termination or reduction of the rate and/or frequency of distraction if sensed conditions proximate the break exceed predetermined programmed values.

11 Claims, 11 Drawing Sheets

PORTABLE BONE DISTRACTION APPARATUS

BACKGROUND OF THE INVENTION AND PRIOR ART

Automated bone distraction apparatus is known but requires regular periodic adjustment by a skilled professional. As reported by Ilizarov in *Clinical Orthopaedics and Related Research*, No. 250, January 1990, the rate and frequency of bone distraction may have to be slowed, speeded up, or even reversed, depending upon the quality of bone formation in the distraction gap, the response of the soft tissues and nerves to elongation, and other considerations. If the distraction rate progresses too quickly, one of the first places it will be noticed is in the blood supply to the distal side of the break. If the blood supply is being compromised due to stretching the soft tissue too rapidly, the temperature of the tissue on the distal side of the break decreases. An additional symptom of hyper-distraction is lower oxygen concentration on the distal side of the distraction.

It is an object of the present invention to provide a bone distraction apparatus which incorporates a portable programmable controller and motor drive which may be carried at all times by the patient and which has appropriate built in safeguards to prevent tissue or bone damage due to distraction at improper rates or frequency of distractions,

SUMMARY OF THE INVENTION

The present invention provides a portable bone distraction apparatus comprising:

a) a motor driven bone distraction mechanism having at least two fasteners for attachment to the proximal and the distal sides of a bone break;

b) a motor for periodically moving said attachments relative to each other to distract the bone;

c) a microprocessor control circuit for controlling the operation of said motor;

d) input means for manually programming the desired rate of bone distraction into said microprocessor;

e) means for sensing a tissue condition parameter and for providing signals representative of the condition of tissue proximate the locations of said bone attachments to said microprocessor;

f) means for comparing said sensed condition signals with a normal condition parameter programmed into said microprocessor; and g) means for adjusting the operation of said motor when said sensed condition signals vary by a predetermined amount from said normal condition parameter programmed into said microprocessor.

BRIEF DESCRIPTION OF THE DRAWING

FIGS. 5A-5I show a preferred system algorithm and flow diagram.

DESCRIPTION OF THE PREFERRED EMBODIMENT

Figures 1, 2, 3:
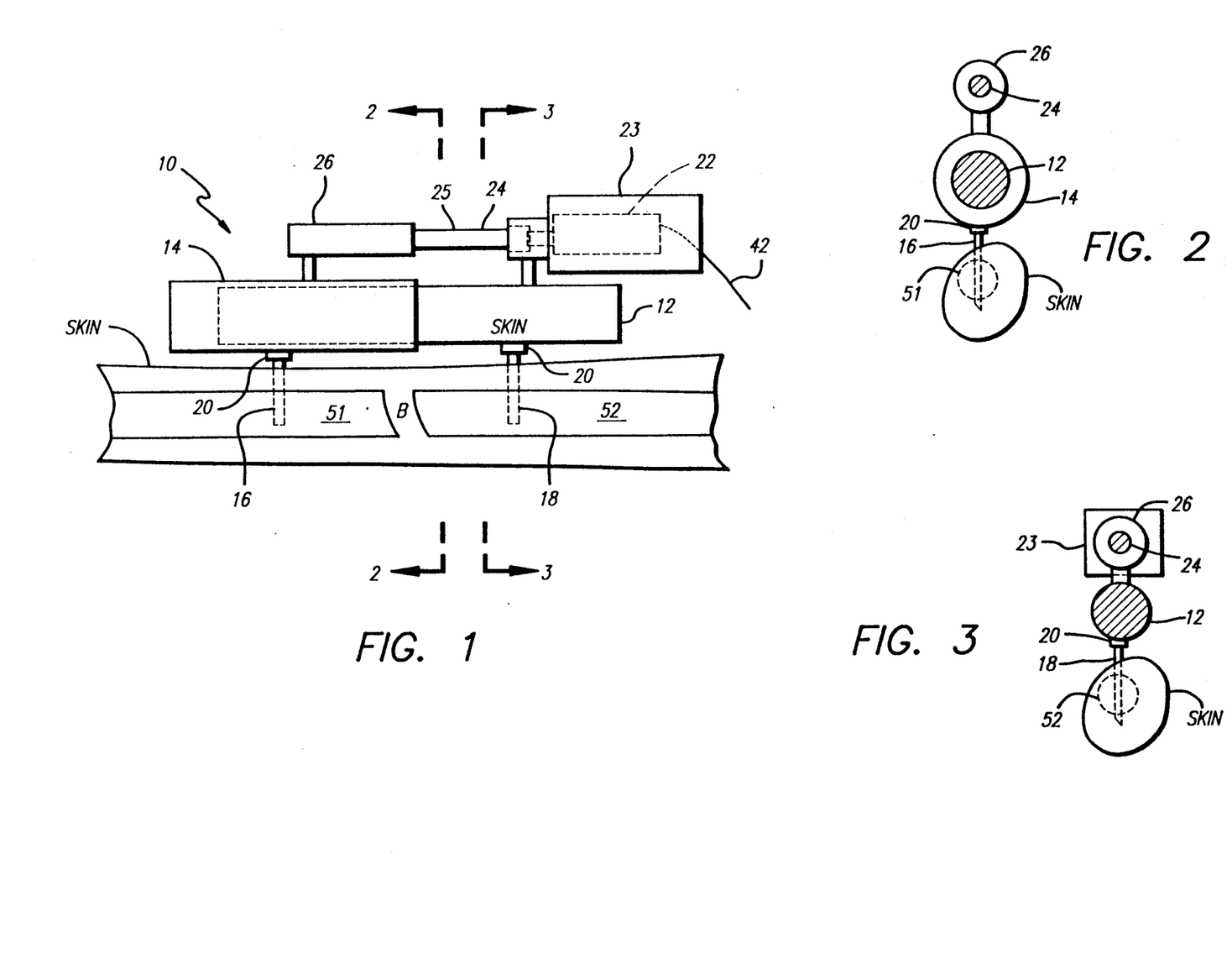
FIG. 1 is a schematic plan view of a portable bone distraction apparatus.
FIG. 2 is a sectional elevation taken at line 2—2 on FIG. 1.
FIG. 3 is a sectional elevation taken at line 3—3 on FIG. 1.

The distraction apparatus comprises a frame 10 having a pair of telescopically moveable parts 12, 14 upon which bone attachment connectors such as pins or screws 16,18 are removeably mounted by conventional fasteners 20. The pins or screws are inserted through the skin and subcutaneous tissue directly into the bone segments (S1, S2) to be distracted on opposite sides of the break (B) which is shown to an enlarged scale for clarity.

The parts 12, 14 of the distraction frame are moved toward and away from each other at a controlled rate of speed and/or frequency of distraction by an electric motor 22. Motor 22 is rigidly affixed to part 12 and an internally threaded member 26 is rigidly affixed to part 14. Motor 22 through a gear reducer not shown, slowly rotates a rod 24 having a threaded end 25 which is received in the threaded member 26 such that the member 26 is axially positionable relative to the rod 24.

An alternative arrangement may employ a non-rotatable rod 24 which has a threaded portion engaged by a rotatable adaptor which is rotated by the motor 22 to axially position the rod relative to the motor, the end of the rod remote from the motor being secured to part 14 whereby part 14 can be positioned relative to part 12.

The relatively moveable parts 12, 14 of the distraction frame are telescopingly interengaged with close sliding tolerance and keyed to prevent relative rotation of part 12 relative to part 14 to maintain precise alignment of the parts and bone attachment pins or screws 16, 18 during distraction.

The motor 22 is preferably a D.C. motor having a reduction gearbox which is contained in a sealed housing which also contains a tach pulse generator 23 (FIG. 4) which generates electrical pulses indicative of the direction and number of rotations of the motor driveshaft, the number and duration of motor inactive intervals, and the number and duration of time intervals during which motor 22 is activated.

Figure 4:
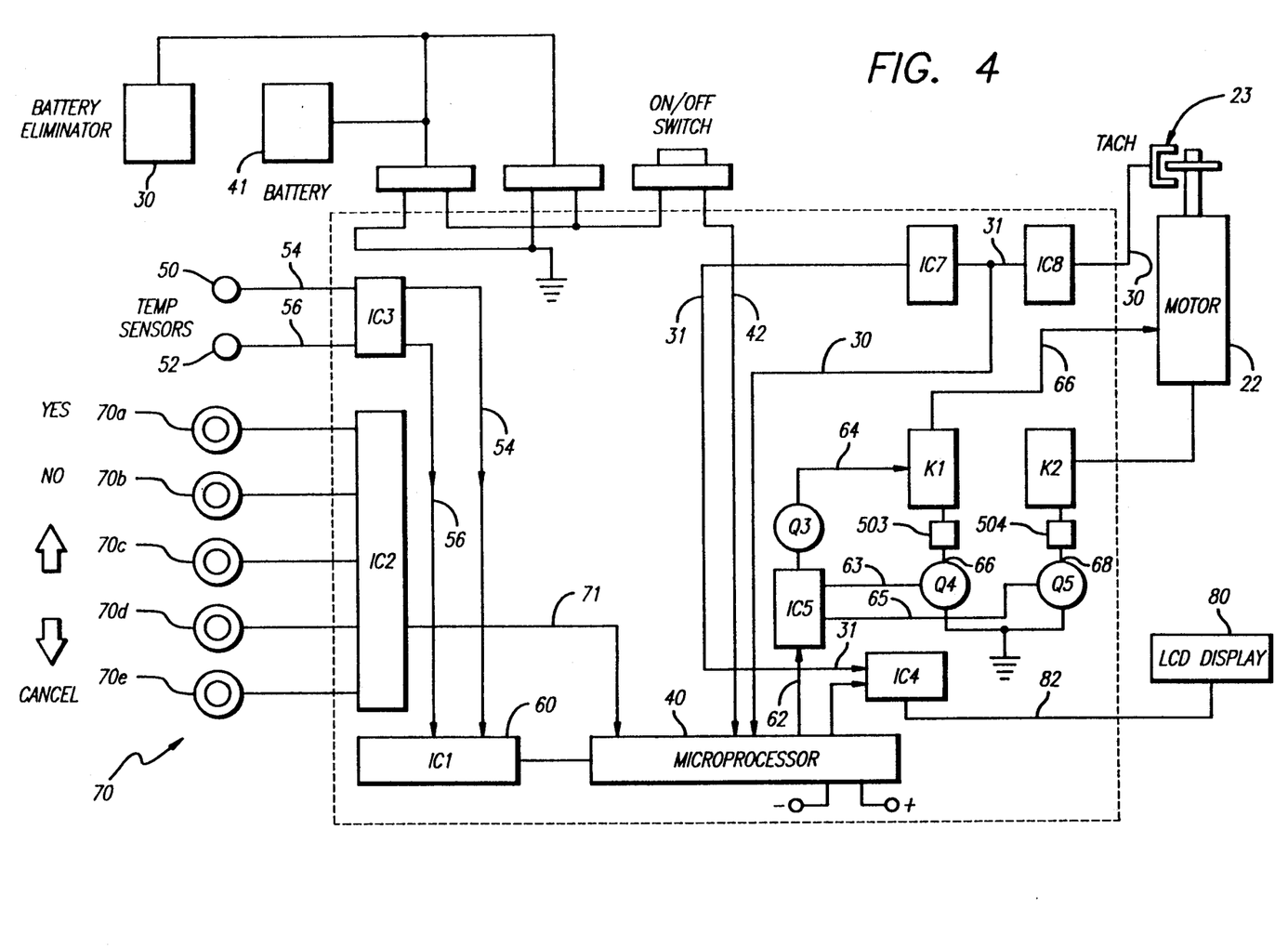
FIG. 4 is a schematic view of the microprocessor signal processing which controls the distraction apparatus of FIG. 1.
Figure 5A:
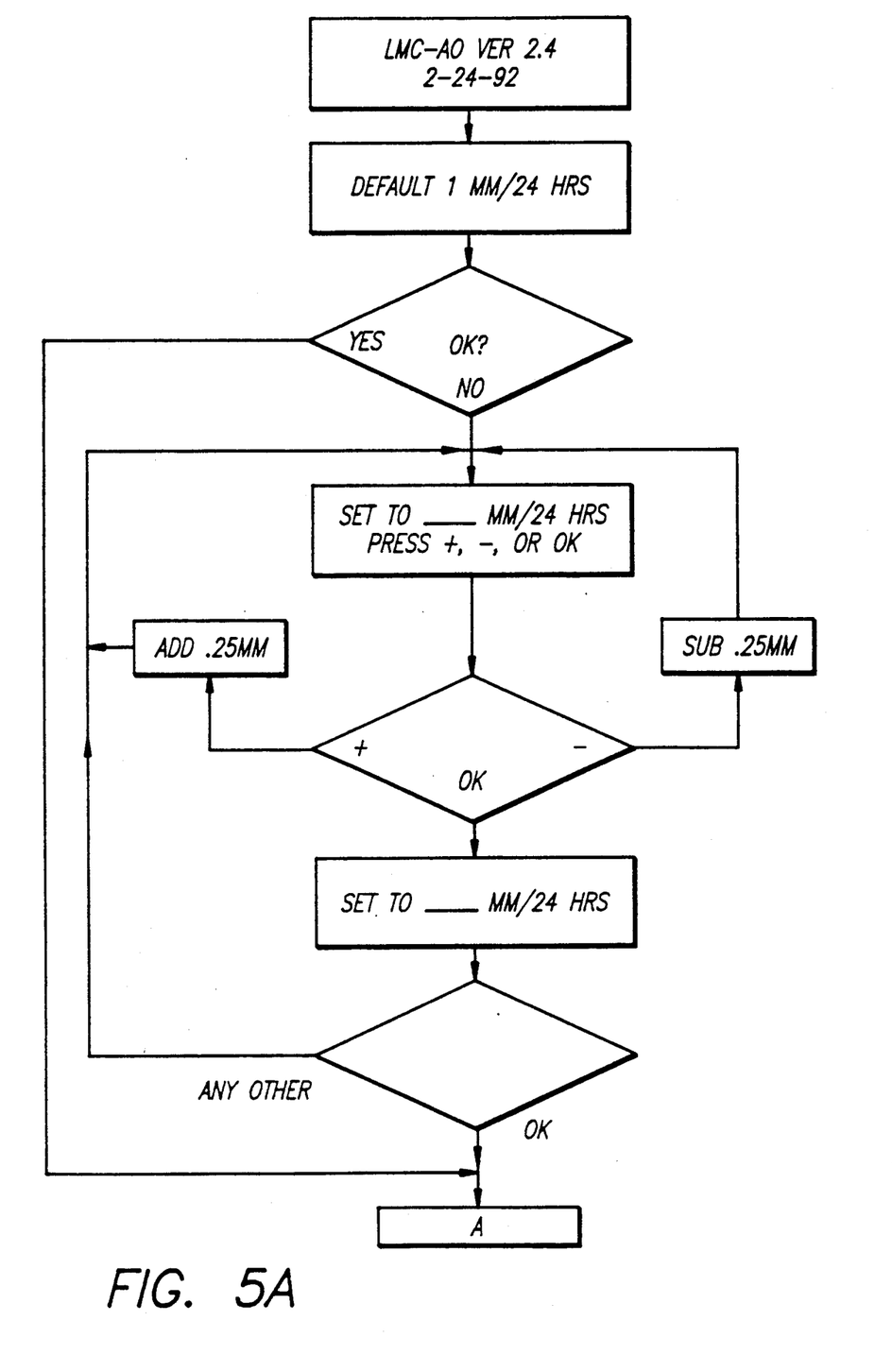
Figure 5B:
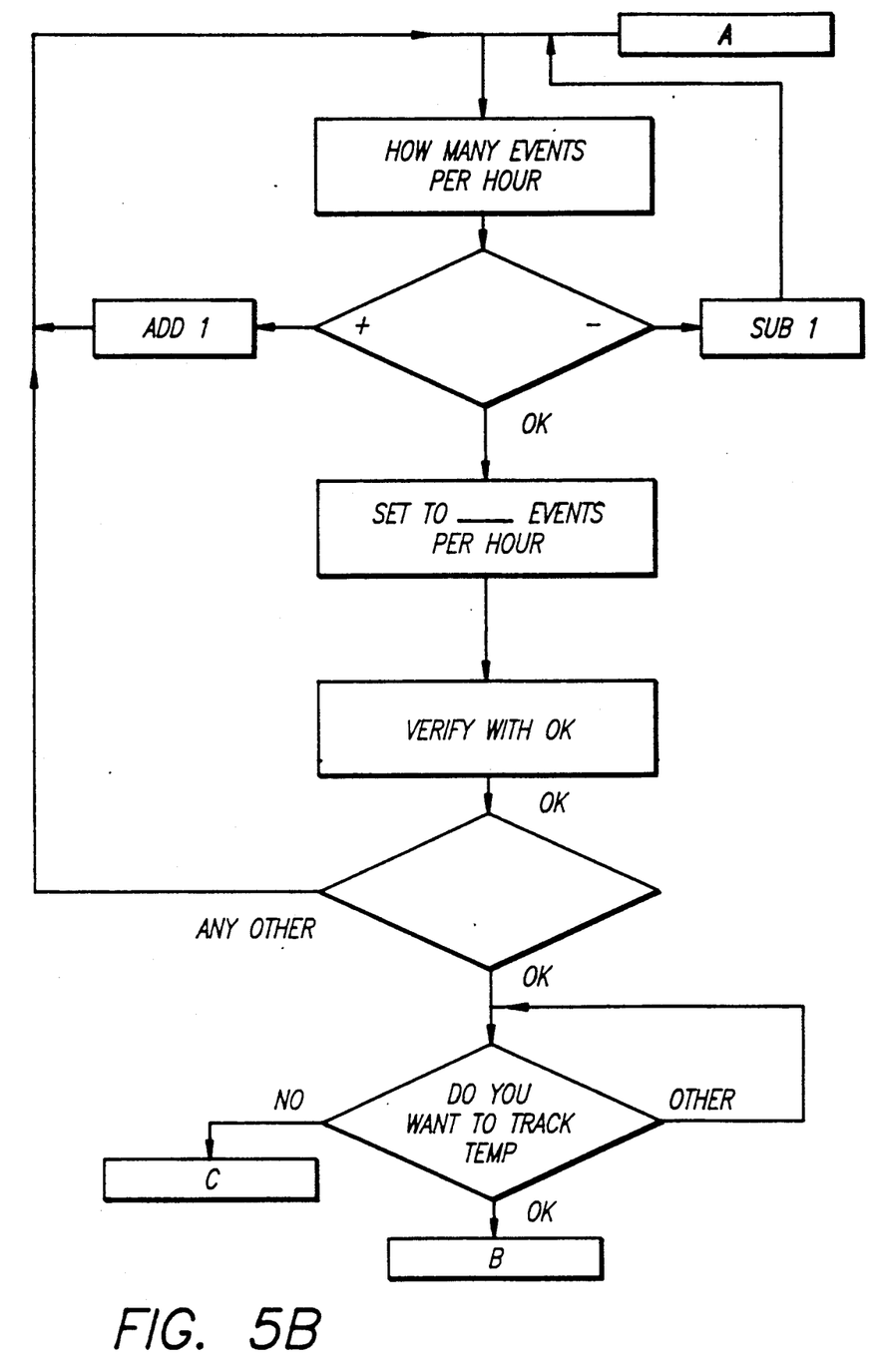
Figure 5C:
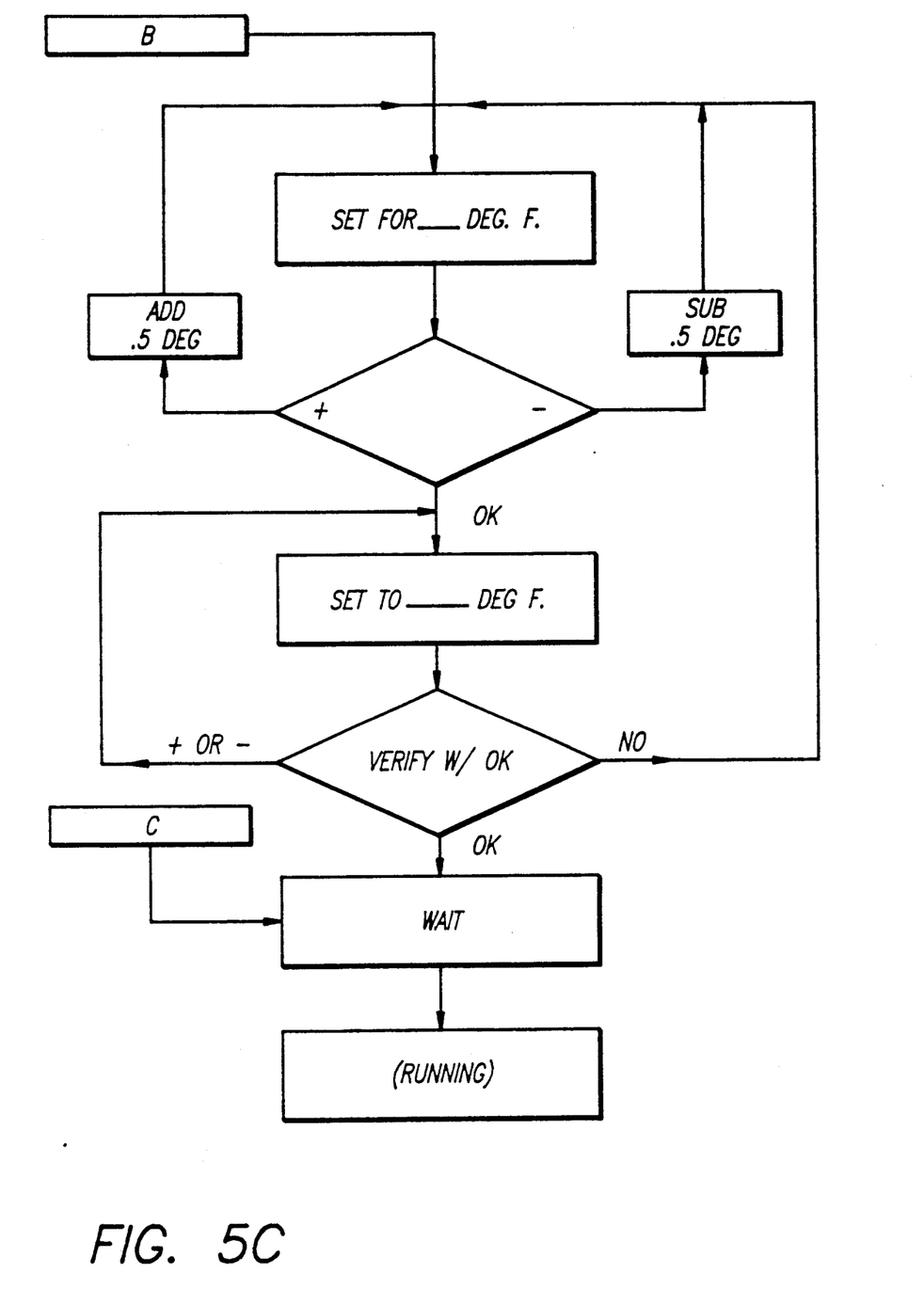
Figure 5D:
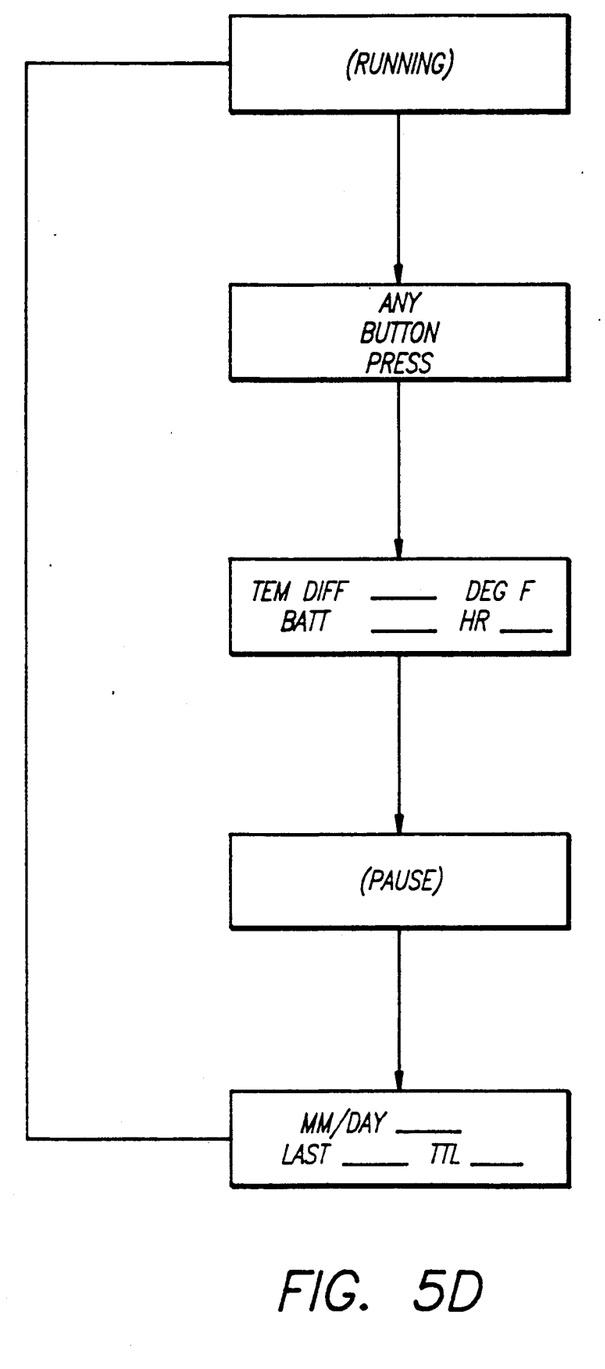
Figure 5E:
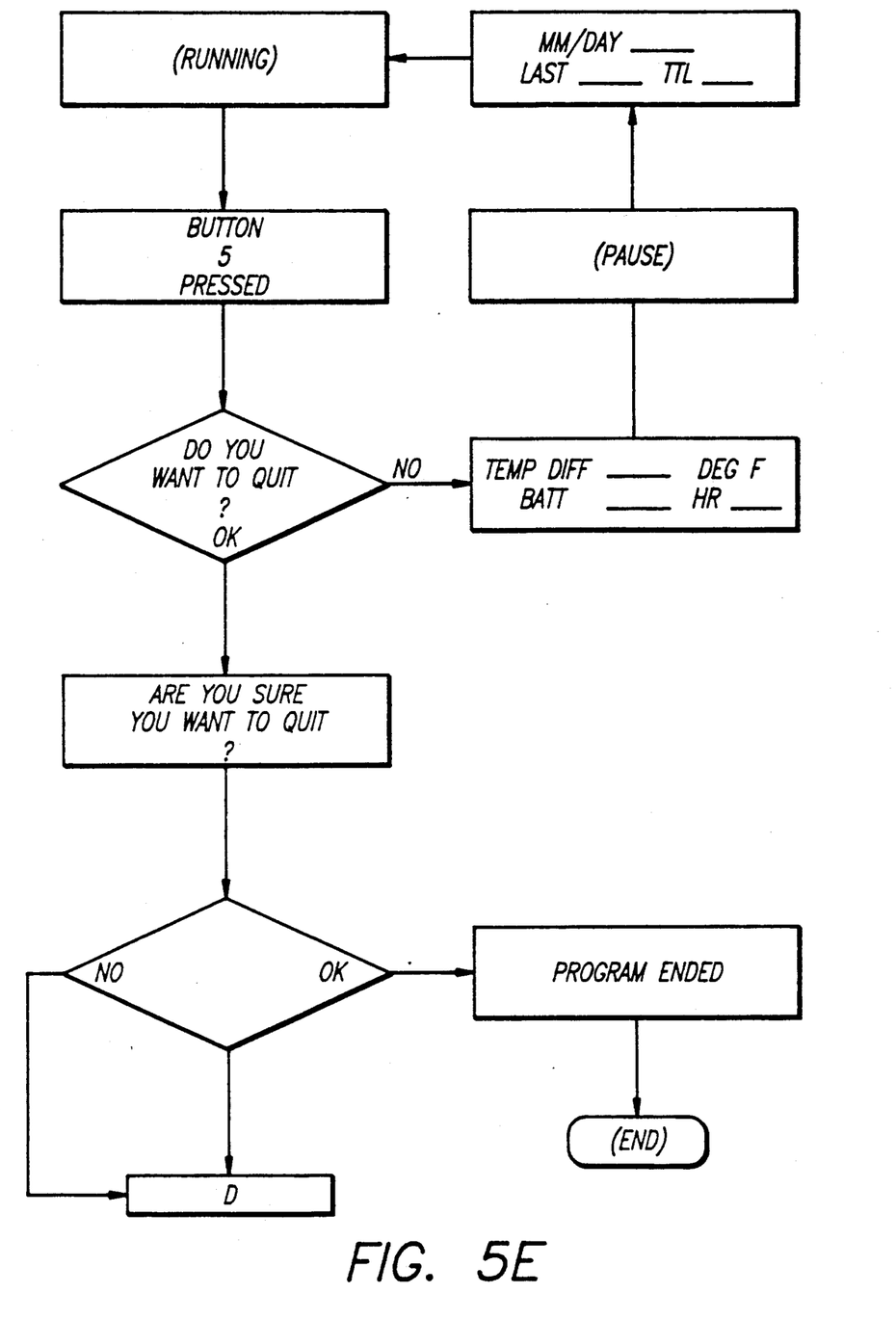
Figure 5F:
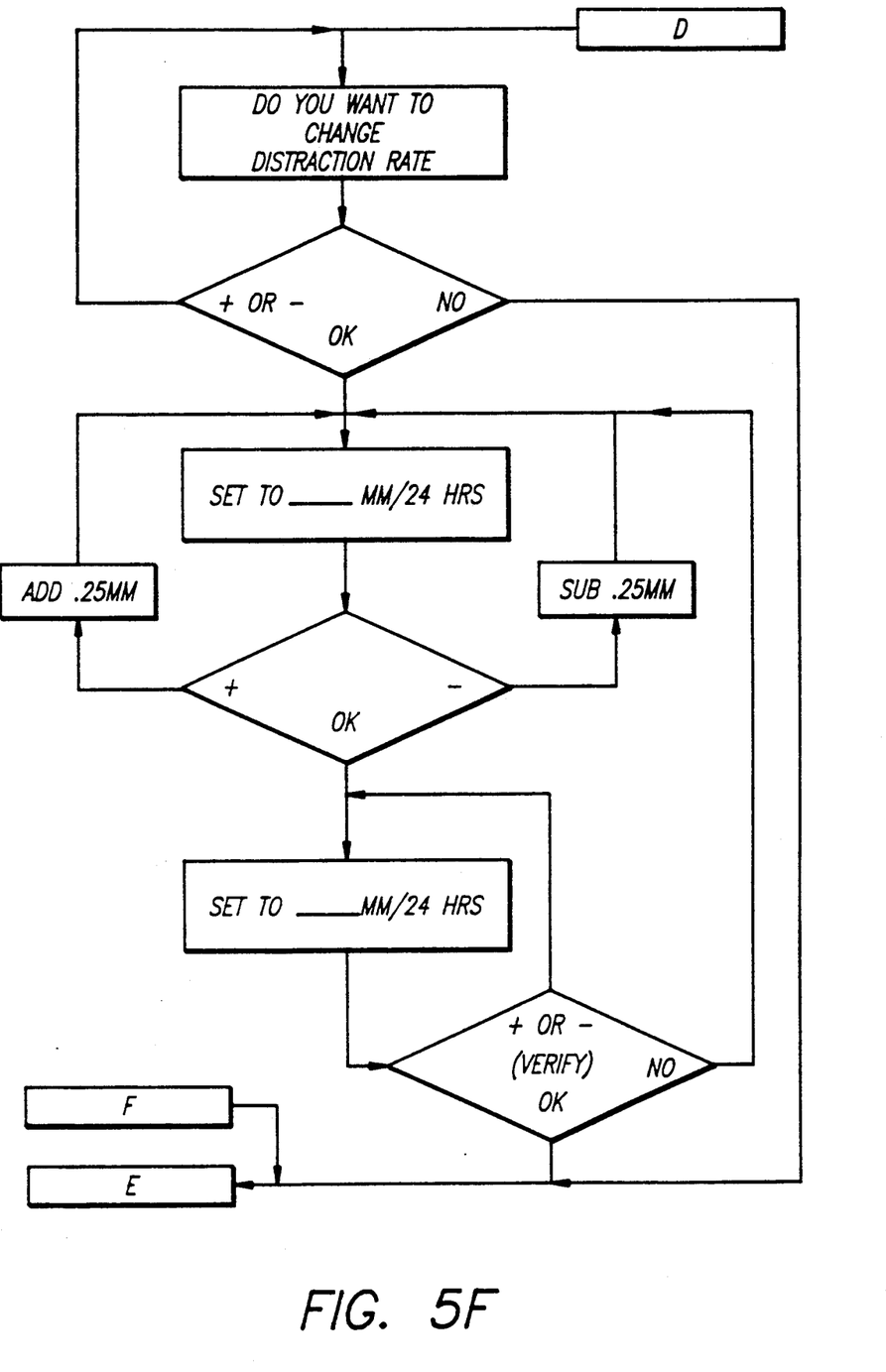
Figure 5G:
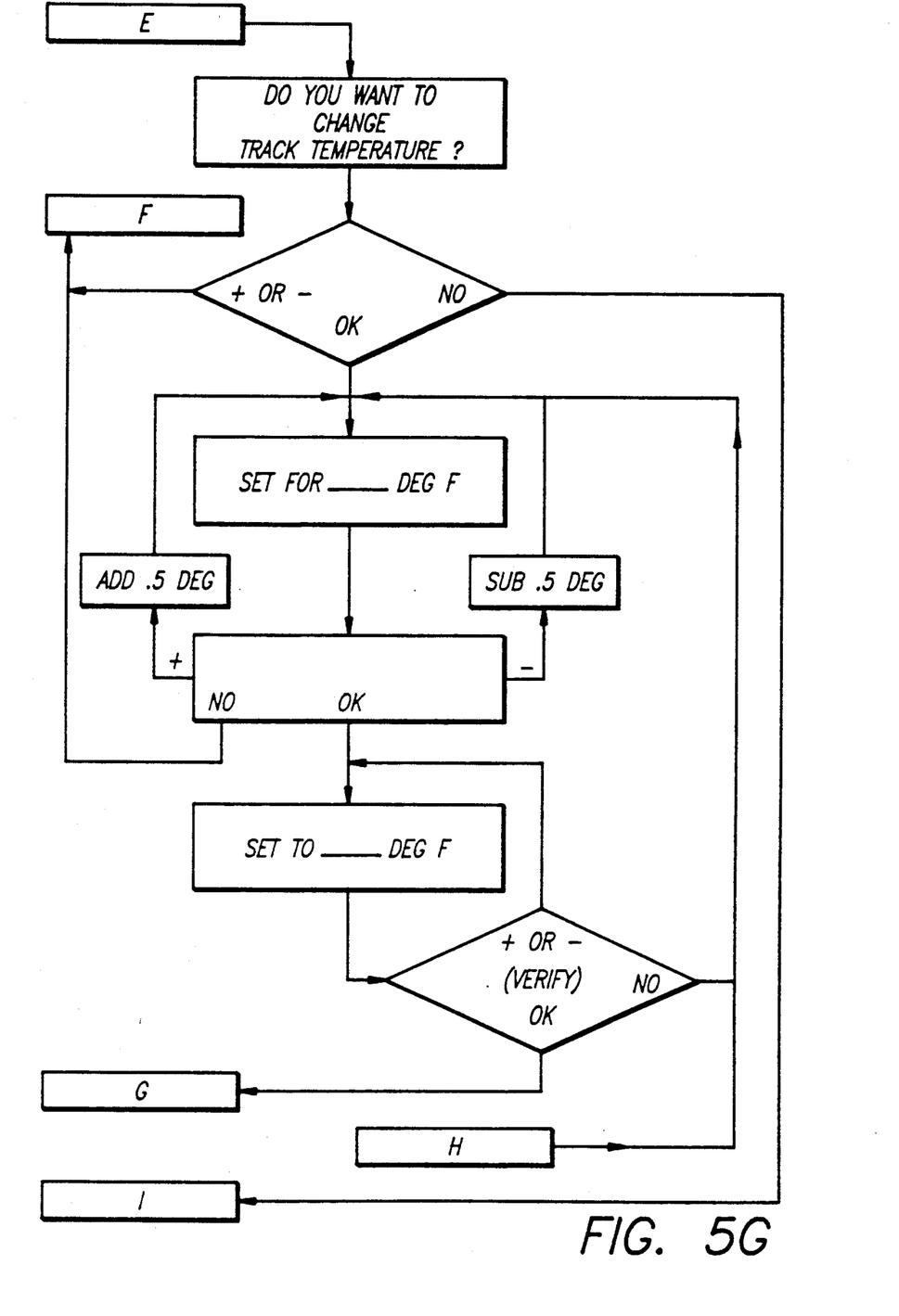
Figure 5H:
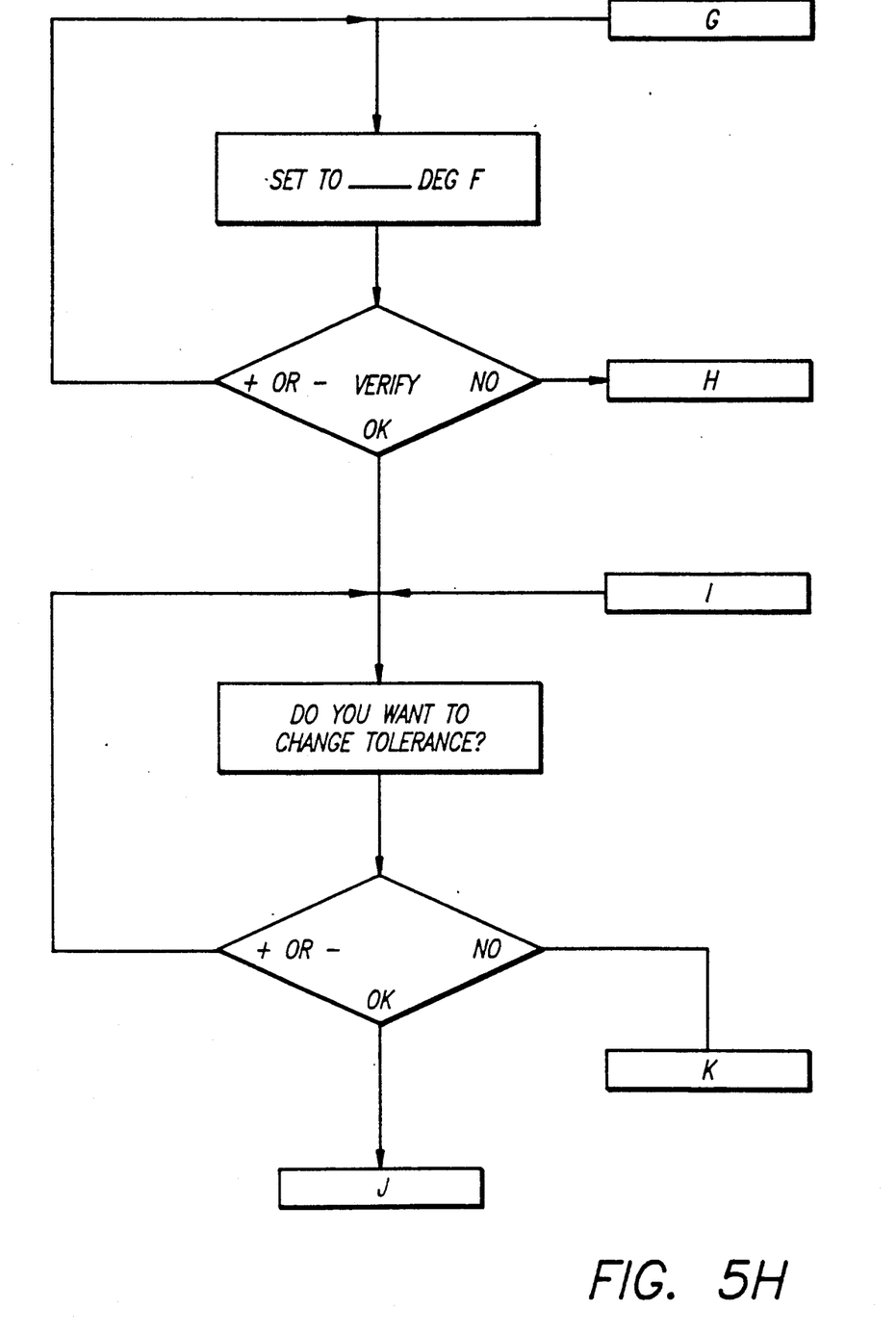

Referring now to FIG. 4, the tach pulses are fed from the motor 22 on line 30 to a counter IC8 and thence to a microprocessor databus 40 on line 30 and to latch IC7 on line 31 and thence to latch IC4. The distraction apparatus including the motor and control circuitry are all miniaturized and contained in a housing adapted to be carried by or worn by the patient. The housing also contains a replaceable source of electrical power in the form of a battery 41 whose output is suitably stepped down and delivered by an ON/OFF switch on line 42 to power the microprocessor and from relay K1 via power line 66 to drive the motor in forward or reverse directions as will be described below.

A pair of probes 50, 52 which sense the desired parameter such as temperature or oxygen content, is placed in the skin or subcutaneous tissue proximate the pins or screws 16, 18 on the proximal and distal sides of the bone break to sense tissue conditions at these locations. The probes 50, 52 each generate an electrical signal indicative of the condition sensed by the probes, the signals being transmitted with amplification at IC3 on lines 54, 56 to an analog/digital converter 60 and then to the microprocessor 40. The lowering of tissue temperatures proximate the distraction is a known precursor of possible tissue damage as is reduced oxygen content. The microprocessor compares the digitized sensor output signals with preprogrammed stored values representative of normal parameters expected at these locations. Programming of the microprocessor 40 is accomplished via a control panel 70 having a plurality of pushbuttons 70a-70e including YES, NO, UP ARROW, DOWN ARROW and CANCEL buttons for enabling the patient or the physician to easily select and increase or decrease the chosen parameter, the chosen data being transmitted to the microprocessor on line 71.

The microprocessor 40 is programmed to generate motor control signals on lines 62, 64, 66 and 68. The signals on line 62 comprise a motor power signal, a motor direction signal (FRW/REV) and a motor on safety signal. The signals are sent first to latch IC5, the motor power signal then being passed to transistor Q3 to control line 64 which provides a ground path for the motor 22. The motor FWD/REV signal is transmitted to transistor Q4 which controls line 66 through diode SD3 to either open or close the motor direction control relay K1 depending on which voltage polarity is needed. The motor safety relay signal is sent from latch IC5 to turn on transistor Q5 which provides a ground path for the motor through line 68 through diode SD4 by turning on safety relay K2. Relays K1 and K2 are connected to pass the FWD/REV and SAFETY control signals from microprocessor 40 to the motor 22 in accordance with soft tissue parameters sensed by sensors 50 and 52 which are compared in microprocessor 40 with the pre-programmed normal value. Upon deviation of the sensed soft tissue parameter beyond the programmed limit, the microprocessor first sends a direction control signal on lines 62, 63 and 66 which reverses the direction of rotation of motor 22 to immediately alleviate the condition and, if necessary, the microprocessor 40 sends a safety signal on lines 62, 65 and 68 to relay K2 to terminate delivery of the electrical power to the motor 22 to terminate distraction.

The control apparatus also includes an LCD screen 80 for selectively displaying various data such as the default distraction rate, e.g. 1 mm/24 hours; the programmed distraction rate; the programmed number of distraction events/hour; the programmed control parameter; the amount of distraction that took place during the last event; and the cumulative total distraction, all of which may be stored for analysis. Data is fed from microprocessor 40 to the LCD screen 80 on line 82 via latch IC4. Preferably the controller is programmed to provide an alarm signal which is intended to both audibly and visually (on the LCD) stimulate the patient to take corrective action or immediately consult his physician.

The microprocessor 40 permits corrective action by the patient himself by enabling him to program or adjust one or more of (1) the rate of continuous distraction, (2) the frequency of discrete time spaced distractions and (3) the duration of discrete time spaced distractions. For example, it may be desired to distract at the rate of 1.0 mm/day. Although conventional practice requires the patient to visit the physician or a technician for periodic adjustments of the distraction frame, it is known that a continuous steady rate of distraction is preferable or, since there is no known continuous automated distraction apparatus, the best approximation is to perform a series of incremental distractions. In general, the greater the number of small incremental distractions, the more benefit to the patient (as compared with fewer but greater incremental distractions) but also the more the patient is inconvenienced if he or she must visit a physician or technician each time. Accordingly the portable automated distraction apparatus disclosed herein is ordinarily programmed to provide continuous bone distraction at the highest tolerable rate of speed so long as sensed tissue parameters do not indicate possible soft tissue damage. Upon sensing excessive variations, the apparatus can be immediately reversed or automatically totally shut off, slowed down or the distraction can be performed incrementally with longer intervals between distractions to allow for sufficient tissue recovery. The possibilities for proper programming of the microprocessor are virtually boundless within the parameters set forth above. Preferably the system includes enough memory to store at least one week of distraction information and data which can be downloaded and transmitted by modem over telephone lines to a control center where the patient's physician or trained technicians can remotely make changes to the variables of the program.

Without limitation, the presently preferred embodiment uses an 80C32 microprocessor with 32 kilobytes of ROM memory and 32 kilobytes of RAM memory. Power may be input to the system from a battery eliminator 90 which may be used to power the system directly from a standard source of AC power, or to charge rechargeable batteries 41. FIGS. 5A-5I show the presently preferred script or system algorithm and a flow diagram thereof which uses tissue temperature as the sensed parameter.

Persons skilled in the art will readily appreciate that various modifications can be made from the preferred embodiment thus the scope of protection is intended to be defined only by the limitations of the appended claims.

I claim:
1. A portable bone distraction apparatus comprising:
 a) a motor driven bone distraction mechanism having at least two fasteners for attachment to the proximal and the distal sides of a bone break;
 b) a motor for periodically moving said attachments relative to each other to distract the bone;
 c) a microprocessor control circuit for controlling the operation of said motor;
 d) input means for manually programming the desired rate of bone distraction into said microprocessor;
 e) means for sensing a tissue condition parameter and for providing signals representative of the condition of tissue proximate the locations of said bone attachments to said microprocessor;
 f) means for comparing said sensed condition signals with a normal condition parameter programmed into said microprocessor; and
 g) means for adjusting the operation of said motor when said sensed condition signals vary by a predetermined amount from said normal condition parameter programmed into said microprocessor.

2. The apparatus of claim 1, wherein said condition sensors provide electrical signals representative of the temperature of tissue at both the distal side and at the proximal side of a bone break.

3. The apparatus of claim 2, further comprising input means for manually programming the distraction intervals at which the position of said attachments is adjusted into said microprocessor.

4. The apparatus of claim 3, further comprising a visual display connected to said microprocessor, said visual display being indicative of the programmed rate of bone distraction, the programmed temperature value and the intervals between bone distraction events.

5. The apparatus of claim 1, wherein said condition sensors provide electrical signals representative of the dissolved oxygen content in tissue at both the distal side and at the proximal side of a bone break.

6. The apparatus of claim 5, further comprising input means for manually programming the distraction intervals at which the position of said attachments is adjusted into said microprocessor.

7. The apparatus of claim 6, further comprising a visual display connected to said microprocessor, said visual display being indicative of the programmed rate of bone distraction, the programmed dissolved oxygen value and the intervals between bone distraction events.

8. The apparatus of claim 4, wherein said mechanism comprises an elongate frame having a pair of relatively moveable parts, said motor comprising a D.C. motor and a reduction gearbox having a rotary output and being affixed to a first one of said parts, a shaft having a threaded portion, a threaded follower mounted on said threaded portion, one of said follower and said threaded shaft being connected to said rotary output to be rotated by said motor, a second one of said frame parts being attached to that one of said follower and threaded shaft that is not connected to said rotary motor output, and said bone attachment means being rigidly affixed one each to said relatively moveable parts of said frame.

9. The apparatus of claim 8, wherein said frame parts are telescopically engaged.

10. The apparatus of claim 7, wherein said mechanism comprises an elongate frame having a pair of relatively moveable parts, said motor comprising a D.C. motor and a reduction gearbox having a rotary output and being affixed to a first one of said parts, a shaft having a threaded portion, a threaded follower mounted on said threaded portion, one of said follower and said threaded shaft being connected to said rotary output to be rotated by said motor, a second one of said frame parts being attached to that one of said follower and threaded shaft that is not connected to said rotary motor output, and said bone attachment means being rigidly affixed one each to said relatively moveable parts of said frame.

11. The apparatus of claim 10, wherein said frame parts are telescopically engaged.

* * * * *